United States Patent
Takagi (10) Patent No.: US 9,823,200 B2
(45) Date of Patent: Nov. 21, 2017

(54) FILLER CONNECTION PART INSPECTION METHOD

(71) Applicants: FUJI SEIKO CO., LTD., Hashima-Shi, Gifu-Ken (JP); FUJI SHOJI CO., LTD., Hashima-Shi, Gifu-Ken (JP)

(72) Inventor: Chikara Takagi, Hashima (JP)

(73) Assignees: FUJI SEIKO CO., LTD. (JP); FUJI SHOJI CO., LTD. (JP)

( * ) Notice: Subject to any disclaimer, the term of this patent is extended or adjusted under 35 U.S.C. 154(b) by 0 days.

(21) Appl. No.: 15/029,417

(22) PCT Filed: Nov. 6, 2013

(86) PCT No.: PCT/JP2013/080036
§ 371 (c)(1),
(2) Date: Apr. 14, 2016

(87) PCT Pub. No.: WO2015/068228
PCT Pub. Date: May 14, 2015

(65) Prior Publication Data
US 2016/0258883 A1 Sep. 8, 2016

(51) Int. Cl.
*G01N 21/95* (2006.01)
*G01B 11/30* (2006.01)
*G01B 11/14* (2006.01)

(52) U.S. Cl.
CPC ............. *G01N 21/95* (2013.01); *G01B 11/14* (2013.01); *G01B 11/303* (2013.01); *G01N 2201/101* (2013.01)

(58) Field of Classification Search
CPC ............. G01N 21/95; G01N 2201/101; G01N 21/8851; G01N 21/9515; G01B 11/303;
(Continued)

(56) References Cited

U.S. PATENT DOCUMENTS 6,138,732 A * 10/2000 Kobayashi .......... B60C 15/0018
152/517
2002/0134910 A1* 9/2002 Kokubu .............. G01M 17/027
250/205
(Continued)

FOREIGN PATENT DOCUMENTS

JP 2003-127249 A 5/2003
JP 2007-76289 A 3/2007
(Continued)

OTHER PUBLICATIONS

International Search Report for Application No. PCT/JP2013/080036 dated Jan. 14, 2014.
(Continued)

*Primary Examiner* — Sang Nguyen
(74) *Attorney, Agent, or Firm* — Tarolli, Sundheim, Covell & Tummino LLP (57) ABSTRACT

Provided is a filler connection part inspection method by which the connection state of both end surfaces of a belt-shaped filler that has been affixed annularly along the outer periphery of a bead core is inspected. The filler connection part inspection method includes a step of obtaining data of the distance between optical sensors and side surfaces of the filler by scanning, at the side surfaces of the filler, sections of the vicinity of the both end surfaces along the tangential direction of the filler over a predetermined scanning range with the optical sensors, a step of repeating the data obtaining step while the positions of the optical sensors are changed along the radial direction of the filler, and a step of comparing the obtained data with reference data that is set in advance.

5 Claims, 7 Drawing Sheets

(58) Field of Classification Search
CPC .. G06T 7/0004; B29D 30/0061; B29D 30/48; B29D 30/0681; B29D 2030/481
See application file for complete search history.

(56) References Cited

U.S. PATENT DOCUMENTS

| | | | |
|---|---|---|---|
| 2010/0126263 A1* | 5/2010 | Brusarosco | B60C 23/0411 73/146 |
| 2011/0155300 A1* | 6/2011 | Takagi | B29D 30/48 156/135 |
| 2011/0188731 A1* | 8/2011 | Sekiguchi | G01B 11/30 382/141 |
| 2012/0211169 A1* | 8/2012 | Honma | B29D 30/48 156/422 |
| 2013/0009078 A1 | 1/2013 | Inoue et al. | |
| 2013/0327458 A1* | 12/2013 | Ohno | B60C 3/06 152/209.1 |
| 2014/0125792 A1 | 5/2014 | Yoshimatsu et al. | |
| 2014/0288689 A1* | 9/2014 | Ballabio | B29D 30/16 700/99 |

FOREIGN PATENT DOCUMENTS

| | | |
|---|---|---|
| JP | 2008-74329 A | 4/2008 |
| JP | 2010-145374 A | 7/2010 |
| WO | WO 2013/012082 A1 | 1/2013 |

OTHER PUBLICATIONS

International Preliminary Report on Patentability for Application No. PCT/JP2013/080036 dated May 10, 2016.
Notification of Reasons for Refusal for Japanese Application No. 2015-546195 dated Jun. 27, 2017.

* cited by examiner

FILLER CONNECTION PART INSPECTION METHOD

RELATED APPLICATIONS

The present invention is a U.S. National Stage under 35 USC 371 patent application, claiming priority to Serial No. PCT/JP2013/080036, filed on 6 Nov. 2013; the entirety of which is incorporated herein by reference.

BACKGROUND OF THE INVENTION

The present invention relates to a method for inspecting a connected portion of a filler in which a strip of a filler is adhered to the outer circumference of a bead core for a vehicle tire, the two end surfaces of the filler are adhered and connected to each other, and then the state of the connected portion is inspected.

Figure 11:
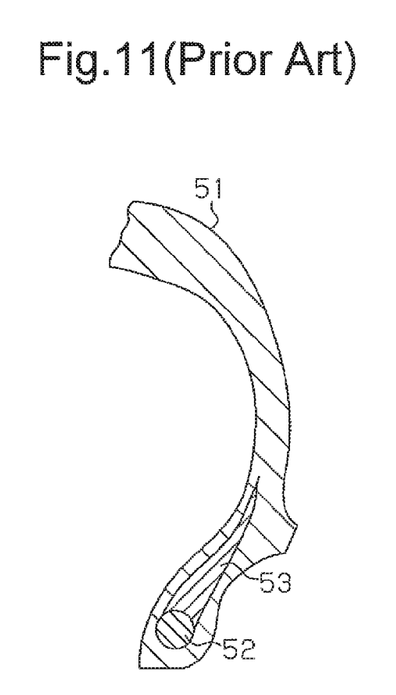
FIG. 11 is a partial cross-sectional view showing a vehicle tire.
Figure 12A:
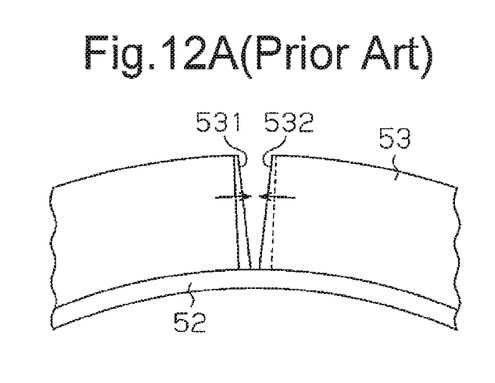
FIGS. 12A and 12B are partial front views showing a method for attaching a filler to a bead core.
Figure 12B:
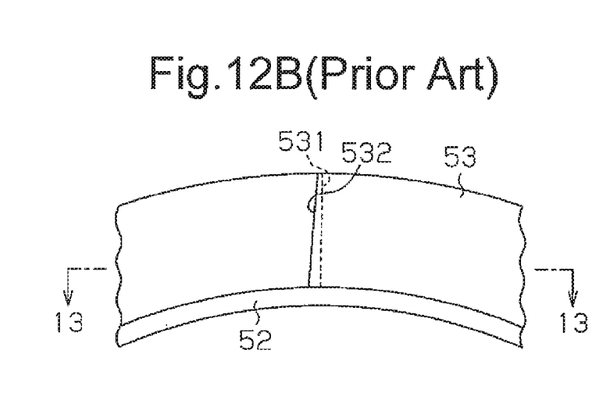
Figure 13:
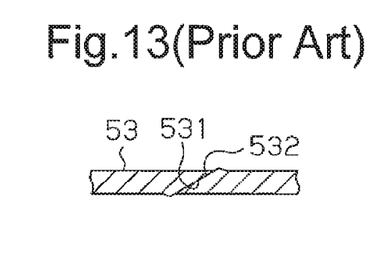
FIG. 13 is a partial enlarged cross-sectional view taken along line 13-13 in FIG. 12.

As shown in FIG. 11, in a typical vehicle tire, an annular bead core 52 and an annular filler 53 are embedded in the inner rim of each of the two sidewalls of a tire rubber 51. A strip of the filler 53 is adhered to the outer circumference of the bead core 52 in advance as shown in FIG. 12A. Then, the two end surfaces 531 and 532 are adhered and connected to each other as shown in FIGS. 12B and 13 so that the filler 53 attached to the bead core 52 becomes annular. Patent document 1 discloses a structure in which a filler is adhered to the outer circumference of a bead core, and the two end surfaces of the filler are connected to each other.

Figure 14A:
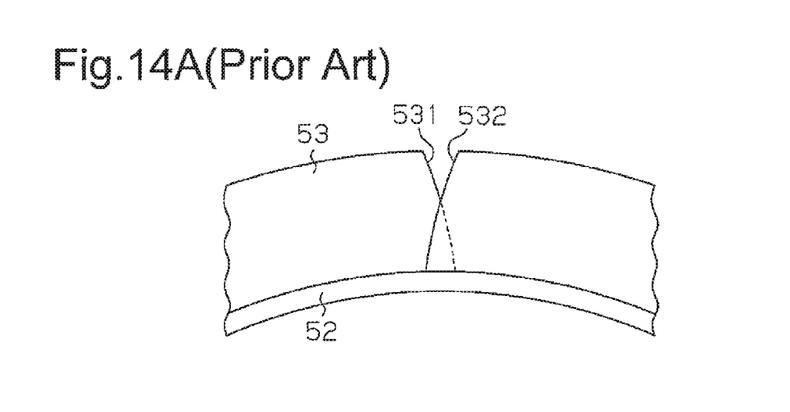
FIGS. 14A to 14C are partial front views showing different connection defects in the two end surfaces of a filler.
Figure 14B:
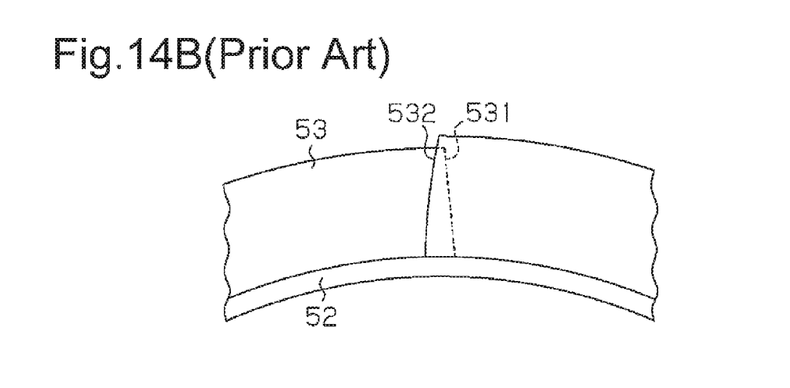
Figure 14C:
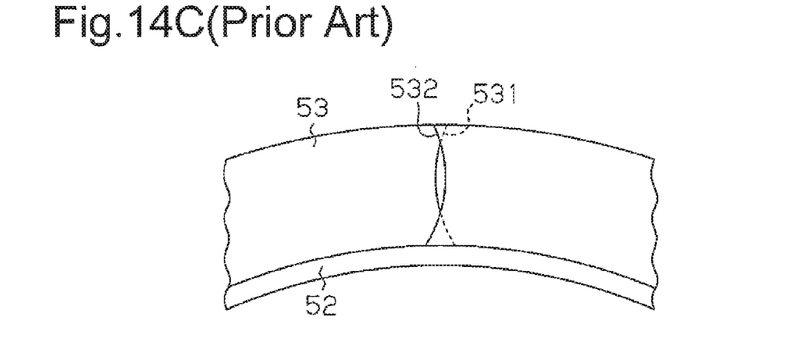
Figure 14D:
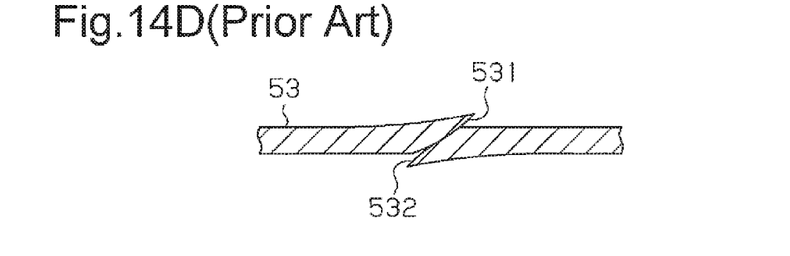
FIG. 14D is a partial cross-sectional view showing a further connection defect.

When the filler 53 is attached to the bead core 52 in this manner, a connection defect may occur at the portion where the two end surfaces 531 and 532 of the filler 53 are connected as shown in FIGS. 14A to 14D. More specifically, FIG. 14A shows a situation in which a gap is formed in the outer circumferential end of the connected portion. FIG. 14B shows a situation in which a step is formed in the outer circumferential end of the connected portion. FIG. 14C shows a situation in which a gap is formed in the middle of the connected portion. FIG. 14D shows a situation in which the end surfaces of the connected portion are displaced in the thickness-wise direction.

PRIOR ART DOCUMENT

Patent Document

Patent Document 1: Japanese Laid-Open Patent Publication No. 2003-127249

SUMMARY OF THE INVENTION

In the prior art, when attaching the filler 53 to the bead core 52, after adhering and connecting the two end surfaces 531 and 532 of the filler 53 to each other, the connected portion is visually checked and inspected by an inspector to find products that have a defective connection as described above.

Patent document 1 discloses a structure for connecting the two end surfaces of a filler but does not disclose how to inspect for defective connections.

In the conventional method for inspecting the connected portion of the filler, an inspector visually inspects the connected portion of the filler 53. Thus, the inspection is difficult. In particular, the filler 53, which has a black color, is difficult to check visually and requires inspection skills. Thus, inspection results cannot be obtained with high accuracy.

Accordingly, it is an object of the present invention to provide a filler connected portion inspection method that allows the state of the connected portion of two end surfaces of a filler to be easily and accurately inspected without requiring skill.

To achieve the above object, one aspect of the present invention provides a filler connected portion inspection method for inspecting a connection state of two end surfaces of a strip of a filler adhered along an outer circumference of a bead core into an annular form. The filler connected portion inspection method includes the steps of obtaining data of a distance from an optical sensor to a side surface of the filler by scanning a portion proximate to the two end surfaces at the side surface of the filler in a tangential direction of the filler over a predetermined scanning range with the optical sensor, repeating the step of obtaining data while changing a position of the optical sensor in a radial direction of the filler, and comparing the obtained data with reference data that is set in advance.

The filler connected portion inspection method allows the connected portion to be easily and accurately inspected through optical scanning without the need for an inspector to visually check the state of the connected portion. Further, the comparison of the data that is obtained through optical scanning with the reference data that is set in advance allows the determination of whether or not the connection is defective to be performed with high accuracy.

DETAILED DESCRIPTION OF THE PREFERRED EMBODIMENTS

First Embodiment

A filler connected portion inspection device according to a first embodiment of the present invention will now be described with reference to FIGS. 1 to 8.

Figure 1:
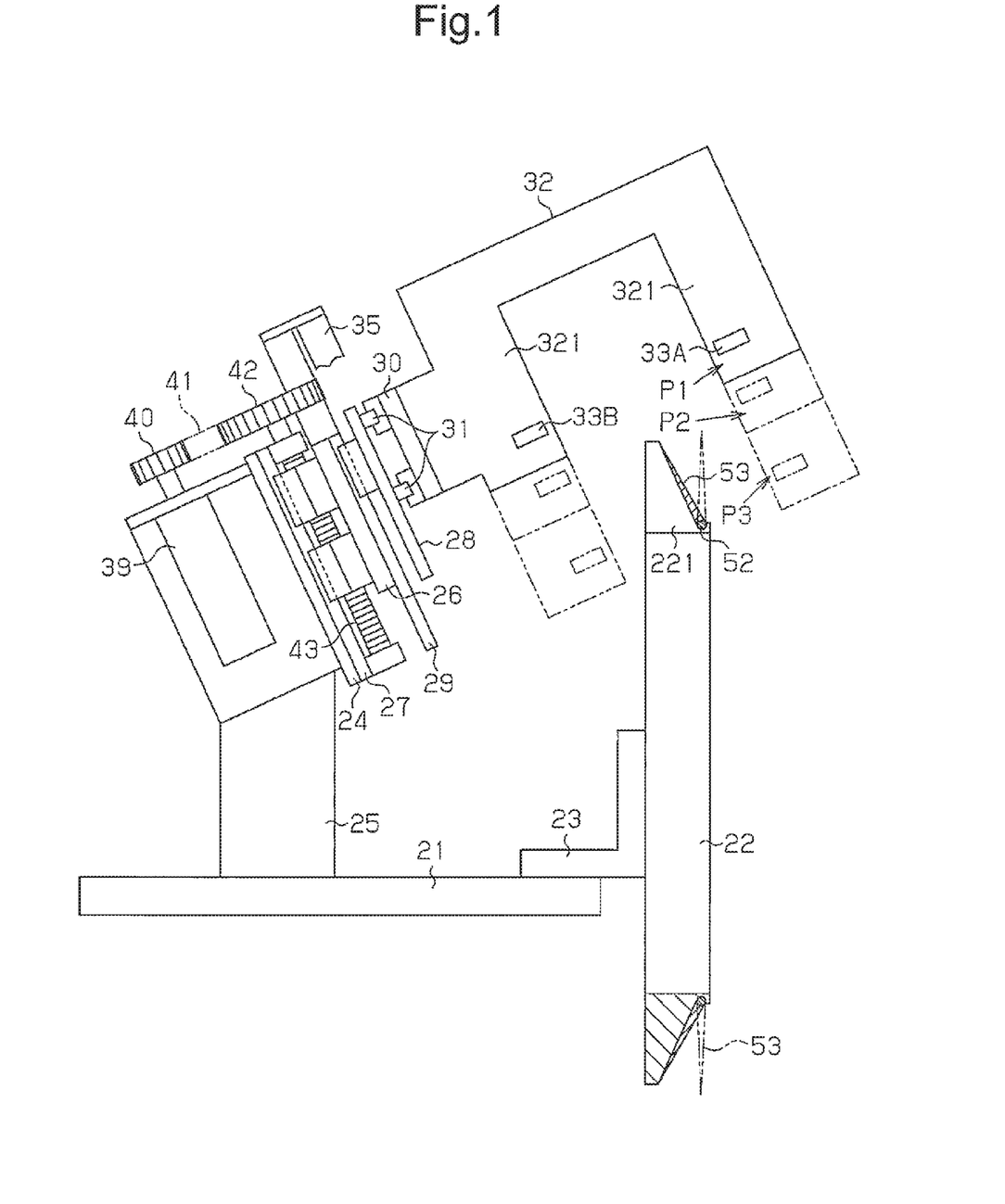
FIG. 1 is a side view showing a first embodiment of a filler connected portion inspection device.
Figure 2:
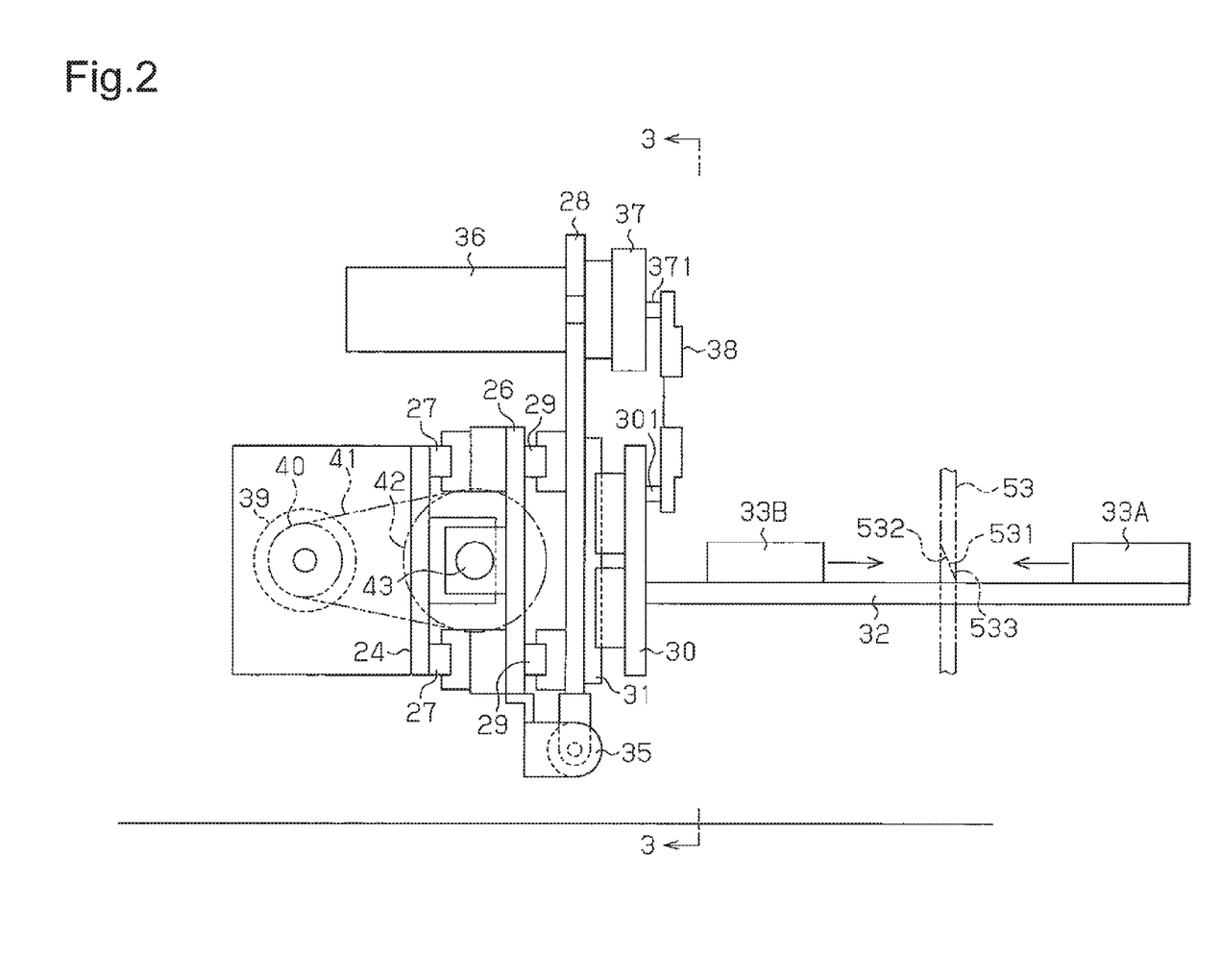
FIG. 2 is an enlarged plan view of the inspection device shown in FIG. 1.
Figure 5A:
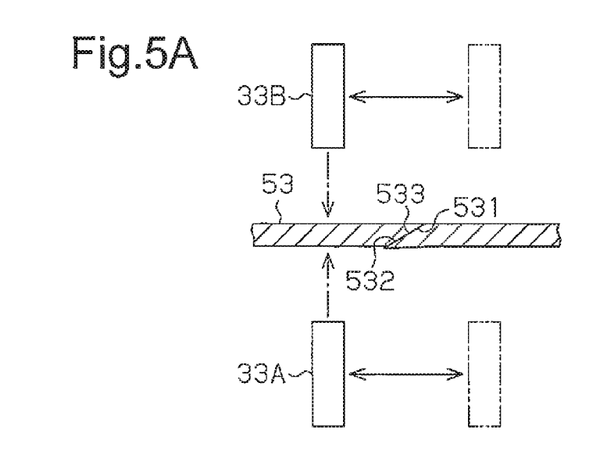
FIG. 5A is an enlarged cross-sectional view taken along line 5-5 in FIG. 4.
Figure 5B:
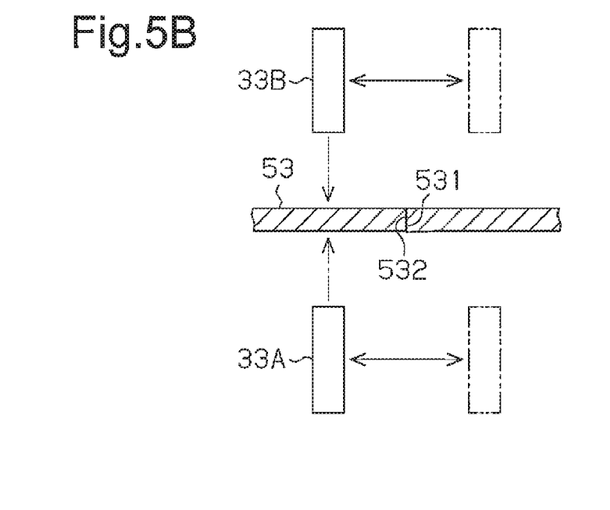
FIG. 5B is an enlarged cross-sectional view of a filler in a further example.

As shown in FIG. 1, a filler connected portion inspection device includes a base 21. A support ring 22 having the shape of a truncated cone is coupled by a bracket 23 to the base 21. The support ring 22 is held so that its center axis extends horizontally. The upper portion of the support ring 22 includes an opening 221 forming by cutting out part of the support ring 22 in the circumferential direction. An annular assembled unit of a bead core 52 and a filler 53 is attached to the outer circumference of the support ring 22. The strip of the filler 53 is adhered to the outer circumference of the bead core 52 in a state inclined relative to the radial direction of the bead core 52. As shown by the double-dashed line in FIG. 1, the filler 53 may be adhered to extend in the radial direction from the bead core 52 instead of being inclined relative to the radial direction. In this state, the two end surfaces 531 and 532 of the filler 53 are adhered and connected to each other. The portion of the filler 53 where the two end surfaces 531 and 532 are connected to each other is arranged in correspondence with where the opening 221 of the support ring 22 is located. Further, as shown in FIGS. 2 and 5A, the end surfaces 531 and 532 of the filler 53 are each defined by an inclined surface 533, which is inclined relative to the thickness-wise direction of the filler 53. In detail, the end surfaces 531 and 532 of the filler 53 are each formed by the inclined surface 533 that is inclined so that the thickness of the filler 53 gradually decreases toward the distal end. The inclined surfaces 533 of the end surfaces 531 and 532 of the filler 53 are opposed to each other and connected. As shown in FIG. 5A, the inclined surfaces 533 are adhered to each other. As shown in FIG. 5B, instead of being inclined, the two end surfaces 531 and 532 of the filler 53 may extend parallel to the thickness-wise direction of the filler 53.

As shown in FIGS. 1 and 2, a support 24 is fixed to the base 21 by a bracket 25. Two first guide rails 27 are fixed to a front surface (right surface as viewed in FIGS. 1 and 2) of the support 24. The first guide rails 27 extend substantially parallel to the direction the filler 53 is inclined in the opening 221 of the support ring 22. A first movable base 26 is supported by the two first guide rails 27 on the support 24 to be movable along the first guide rails. Two second guide rails 29 extending parallel to the first guide rails 27 are fixed to the front surface of the first movable base 26. A second movable base 28 is supported by the second guide rails 29 on the first movable base 26 to be movable along the second guide rails 29. Thus, the second movable base 28 is movable in the same direction as the first movable base 26.

Two third guide rails 31, which extend perpendicular to the direction the first rails guides 27 extend, are fixed to the front surface of the second movable base 28. A third movable base 30 is supported by the third guide rails 31 on the second movable base 28 to be movable along the third guide rails 31. The third movable base 30 is movable in a direction perpendicular to the movement direction of the first movable base 26 and the second movable base 28. More specifically, the third movable base 30 is movable in the tangential direction of the filler 53 in the opening 221 of the support ring 22. A scanning member 32 is fixed to the front surface of the third movable base 30. The scanning member 32 has a substantially C-shaped form in a side view and includes two arms 321, one at the front and one at the rear. The arms 321 of the scanning member 32 respectively support optical sensors 33A and 33B, which are of a laser light type. The optical sensors 33A and 33B respectively oppose the two side surfaces of the connected portion of the filler 53 through the opening 221 of the support ring 22. The scanning member 32 is inclined in correspondence with the filler 53 that is inclined. The scanning member 32 is not inclined when the filler 53 is not inclined as shown by the double-dashed line in FIG. 1.

As shown in FIGS. 1 and 2, a movement cylinder 35, which is located on the first movable base 26, includes a piston rod coupled to the second movable base 28. The movement cylinder 35 is actuated to move the second movable base 28 along the second guide rails 29. This moves the optical sensors 33A and 33B, which are supported by the scanning member 32, between a separated position P1, which is where the optical sensors 33A and 33B are separated upward from the connected portion of the filler 53 as shown by the solid lines in FIG. 1, and an inspection initiation position P2, which is where the optical sensors 33A and 33B are located in correspondence with the outer circumference of the filler 53.

Figure 3:
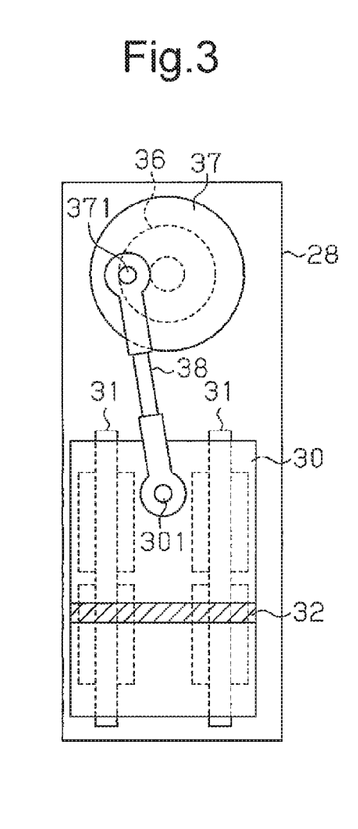
FIG. 3 is a cross-sectional view taken along line 3-3 in FIG. 2.
Figure 4:
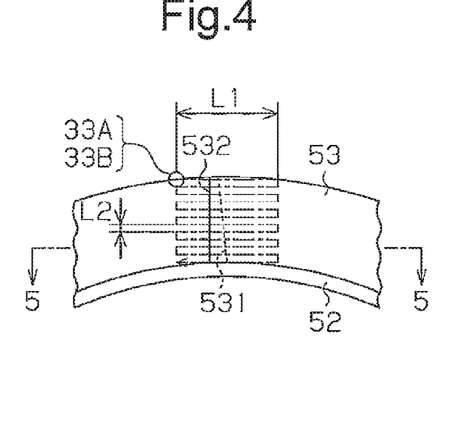
FIG. 4 is a partial front view showing optical scanning performed on a connected portion of a filler by an optical sensor.

As shown in FIGS. 2 and 3, a reciprocation motor 36 is arranged on the second movable base 28. A rotary disk 37 is fixed to the motor shaft of the reciprocation motor 36. The rotary disk 37 includes an eccentric crank pin 371. The third movable base 30 includes a connection pin 301. A crank rod 38 connects the crank pin 371 of the rotary disk 37 to the connection pin 301 of the third movable base 30. The reciprocation motor 36 rotates the rotary disk 37. The crank rod 38 converts rotation of the rotary disk 37 to reciprocation of the third movable base 30 along the third guide rails 31. This reciprocates the optical sensors 33A and 33B, which are supported by the scanning member 32, within a predetermined width in the tangential direction of the filler 53 at opposite sides of the filler 53. Referring to FIG. 4, the optical sensors 33A and 33B perform linear optical scanning on the portion of the filler 53 proximate to the connected portion from opposite sides of the filler 53 over a predetermined scanning range L1 in the tangential direction of the filler 53. The optical sensors 33A and 33B each detect the distance to the corresponding side surface of the filler 53 to obtain data of the distance.

As shown in FIGS. 1 and 2, a pitch-feed motor 39 and a ball screw 43, which extends parallel to the first guide rails 27, are arranged on the support 24. A drive pulley 40 is fixed to the motor shaft of the pitch-feed motor 39. A driven pulley 42 is fixed to the ball screw 43. A timing belt 41 runs around the drive pulley 40 and the driven pulley 42. The first movable base 26 is formed to be engaged with the ball screw 43. The pitch-feed motor 39 generates rotation that rotates the ball screw 43 through the drive pulley 40, the timing belt 41, and the driven pulley 42. The rotation of the ball screw 43 moves the first movable base 26 along the first guide rails 27. The movement of the first movable base 26 changes the positions of the optical sensors 33A and 33B, which are supported by the scanning member 32, in the radial direction of the filler 53. When the optical sensors 33A and 33B reach each of the two ends of the scanning range L1, the first movable base 26 is moved to move the optical sensors 33A and 33B by a predetermined feed pitch L2 in the radial direction of the filler 53. Consequently, as shown in FIG. 4, the optical sensors 33A and 33B repetitively perform optical scanning while changing positions by moving over a predetermined feed pitch L2 in the radial direction of the filler 53 from the inspection initiation position P2 to an inspection completion position P3, which are shown by broken lines in FIG. 1.

The configuration for controlling the filler connected portion inspection device will now be described.

Figure 8:
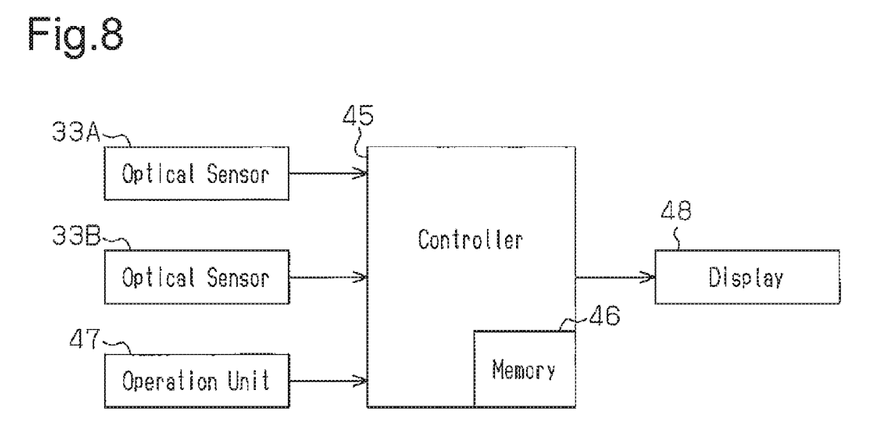
FIG. 8 is a block diagram showing the configuration for controlling the filler connected portion inspection device.

As shown in FIG. 8, the filler connected portion inspection device includes a controller 45 that controls the operation of the entire inspection device. Programs used to control the operation of the inspection device and data used to execute the programs are stored in a memory 46. The controller 45 is connected to the optical sensors 33A and 33B, an operation unit 47, and a display 48. The controller 45 receives, from the optical sensors 33A and 33B, data of the distance from each of the optical sensors 33A and 33B to the corresponding side surface of the filler 53. The controller 45 also receives operation command signals from the operation unit 47. The controller 45 sends, to the display 48, the data obtained by the optical sensors 33A and 33B and determination data of whether or not the connection is defective in the filler 53. The data is shown on the display 48.

Figure 6:
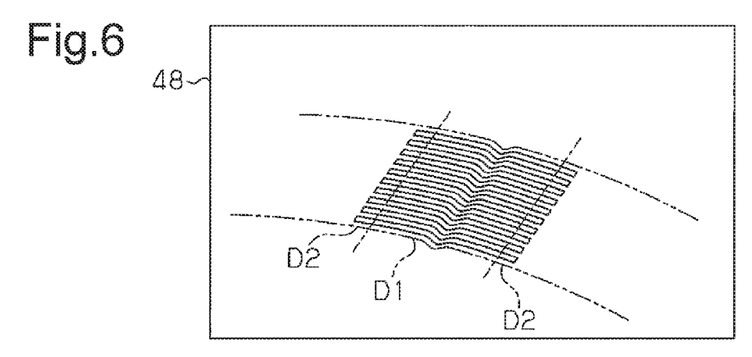
FIG. 6 is a diagram showing data for the vicinity of the connected portion in the filler obtained through optical scanning.

When the controller 45 receives data of the vicinity of the connected portion of the filler 53 from the optical sensors 33A and 33B, the controller 45 shows an image of the data on the display 48. Further, the controller 45 compares the data with reference data, which is stored in advance in the memory 46, and determines whether or not the connection of the two end surfaces 531 and 532 of the filler 53 is defective. Referring to FIG. 6, in this case, it is preferred that the controller 45 exclude data D2 obtained at the two ends of the scanning range L1 and use only data D1 obtained at the middle of the scanning range L1.

Figure 7:
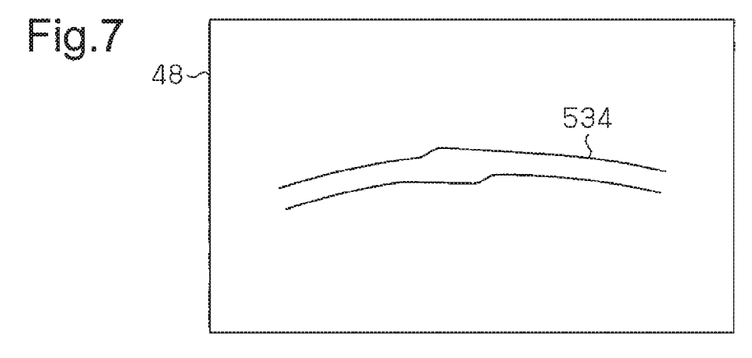
FIG. 7 is a diagram showing the cross-sectional shape of the filler derived from the data obtained in the vicinity of each connected portion at the two side surfaces of the filler.

When the controller 45 receives an operation command signal from the operation unit 47 for checking the cross-section state of the filler 53, the controller 45 obtains the cross-sectional shape of the connected portion from the data obtained by scanning the two side surfaces of the filler 53. Then, the controller 45 shows an image of the cross-sectional shape 534 on the display 48. Further, the controller 45 compares the obtained cross-sectional shape with a reference shape stored in advance in the memory 46 to check the cross-section and determine whether or not the connection is defective.

A method for inspecting the connection of the two end surfaces 531 and 532 of the filler 53 with the filler connected portion inspection device will now be described.

In the filler connected portion inspection device, prior to an inspection, the piston rod of the movement cylinder 35 is retracted and the second movable base 28 is moved toward the upper side as viewed in FIG. 1. Thus, the optical sensors 33A and 33B, which are supported by the scanning member 32, are located at the upper separated position P1 as shown by the solid lines in FIG. 1. Under this situation, a strip of the filler 53 is adhered to the outer circumference of the bead core 52, which is supported by the outer circumference of the support ring 22, into an annular form. Then, a device (not shown) presses the opposite sides of the filler 53 to adhere and connect the two end surfaces 531 and 532 of the filler 53 to each other. Here, the portion of the filler 53 where the two end surfaces 531 and 532 are connected is arranged in correspondence with the position of the opening 221 in the support ring 22.

Then, the connection state of the filler 53 is inspected with the filler connected portion inspection device.

The piston rod of the movement cylinder 35 is projected to move the second movable base 28 to the lower side as viewed in FIG. 1. This moves the optical sensors 33A and 33B, which are supported by the scanning member 32, from the separated position P1, which is shown by the solid lines in FIG. 1, to the inspection initiation position P2, which is shown by the broken lines. As a result, the two optical sensors 33A and 33B are respectively opposed to the two side surfaces of the outer circumferential end of the connected portion of the filler 53 through the opening 221 of the support ring 22.

When the optical sensors 33A and 33B are located at the inspection initiation position P2, the reciprocation motor 36 generates rotation that rotates the rotary disk 37. The crank rod 38 converts rotation of the rotary disk 37 to reciprocation of the third movable base 30 along the third guide rails. This reciprocates the optical sensors 33A and 33B, which are supported by the scanning member 32, within a predetermined width in the tangential direction of the filler 53 at opposite sides of the filler 53. Referring to FIG. 4, the optical sensors 33A and 33B perform linear optical scanning on the portion of the filler 53 proximate to the connected portion from opposite sides of the filler 53 over a predetermined scanning range L1 in the tangential direction of the filler 53. The optical sensors 33A and 33B each detect the distance to the corresponding side surface of the filler 53 and obtain data of the distance.

Whenever the optical sensors 33A and 33B, which are supported by the scanning member 32, reach each of the two ends of the scanning range L1, the pitch-feed motor 39 generates rotation. The rotation of the pitch-feed motor 39 is transmitted by the drive pulley 40, the timing belt 41, and the driven pulley 42 to the ball screw 43. This rotates the ball screw 43. As the ball screw 43 rotates, the first movable base 26 is intermittently moved toward the lower side as viewed in FIG. 1. Consequently, as shown in FIG. 4, the optical sensors 33A and 33B repetitively perform optical scanning, while being moved by the predetermined feed pitch L2 in the radial direction of the filler 53, to change positions from the inspection initiation position P2 to the inspection completion position P3, which are shown by broken lines in FIG. 1.

In this manner, the optical sensors 33A and 33B perform optical scanning on the connected portion of the filler 53 until reaching the inspection completion position P3 and send the scan data of the vicinity of the connected portion to the controller 45. When the controller 45 receives the data, the controller 45 shows an image of the data on the display 48 as shown in FIG. 6. Further, the controller 45 compares the data with the reference data stored in the memory 46 and determines whether or not the connection of the two end surfaces 531 and 532 of the filler 53 is defective. The determination result is shown on the display 48. In this case, as shown in FIG. 6, the data D2 obtained at the two ends of the scanning range L1 is excluded, and only the data D1 obtained at the middle of the scanning range L1 is used for the comparison and determination.

Further, when the controller 45 receives an operation command signal from the operation unit 47 for checking the cross-section of the filler 53, the controller 45 obtains the cross-sectional shape of the connected portion from the data obtained by scanning the two side surfaces of the filler 53. Then, the controller 45 shows an image of the cross-sectional shape on the display 48. Further, the controller 45 compares the obtained cross-sectional shape with the reference shape stored in the memory 46 to check the cross-section and determine whether or not the connection is defective.

When determined that the connected portion of the filler 53 includes a defective connection such as that shown in FIGS. 14A to 14D (non-connected part included or two end surfaces 531 and 532 displaced relative to each other in the radial direction or the circumferential direction), the determination is shown on the display 48 to notify the inspector. In this case, for example, a buzzer may be used to present the notification.

Accordingly, the first embodiment has the advantages described below.

(1) In the first embodiment, a strip of the filler 53 is adhered along the outer circumference of the bead core 52 into an annular form, and the two end surfaces 531 and 532 of the filler 53 are adhered to each other. Then, the state of the connected portion is inspected. In this case, the optical sensors 33A and 33B scan the vicinity of the portion where the two end surfaces 531 and 532 of the filler 53 are connected at the sides of the filler 53 over the predetermined scanning range in the tangential direction of the filler 53. Here, a step of obtaining data of the distance from the optical sensors 33A and 33B to the corresponding side surfaces of the filler 53 is performed. As the positions of the optical sensors 33A and 33B change in the radial direction of the filler 53, the step of obtaining data is repeated. Then, the obtained data is compared with the reference data, which is set in advance.

Thus, the filler connected portion inspection method allows the connected portion to be easily and accurately inspected through optical scanning without the need for an inspector to visually check the state of the connected portion. Further, the comparison of the data that is obtained through optical scanning with the reference data that is set in advance allows the determination of whether or not the connection is defective to be performed with high accuracy.

(2) In the first embodiment, the two end surfaces 531 and 532 of the filler 53 are inclined relative to the thickness-wise direction of the filler 53. This ensures a large area of contact between the two end surfaces 531 and 532 of the filler 53 and reduces defective contact where the two end surfaces 531 and 532 contact each other.

(3) In the first embodiment, optical scanning is performed on the two side surfaces of the filler 53. This allows the state of the two side surfaces at the connected portion of the filler 53 to be simultaneously inspected.

(4) In the first embodiment, the cross-sectional shape at the vicinity of the two end surfaces 531 and 532 of the filler 53 is derived from the data obtained from the two side surfaces of the filler 53. Then, the derived cross-sectional shape is compared with the reference shape that is set in advance. Thus, the comparison of the cross-sectional shape, which is based on the data of the two side surfaces of the filler 53 obtained by the optical sensors 33A and 33B, with the reference shape, which is set in advance, allows the determination of whether or not the connection is defective to be performed with high accuracy.

(5) In the first embodiment, the data D2 obtained at the two ends of the scanning range L1 is excluded. Only the data D1 obtained at the middle of the scanning range L1 is used. This allows the determination of whether or not the connection is defective to be accurately performed. Accordingly, the data amount of the inspected subject can be reduced, and the speed for processing the inspection can be increased.

Second Embodiment

A second embodiment of a filler connected portion inspection method will now be described focusing on differences from the first embodiment.

Figure 9:
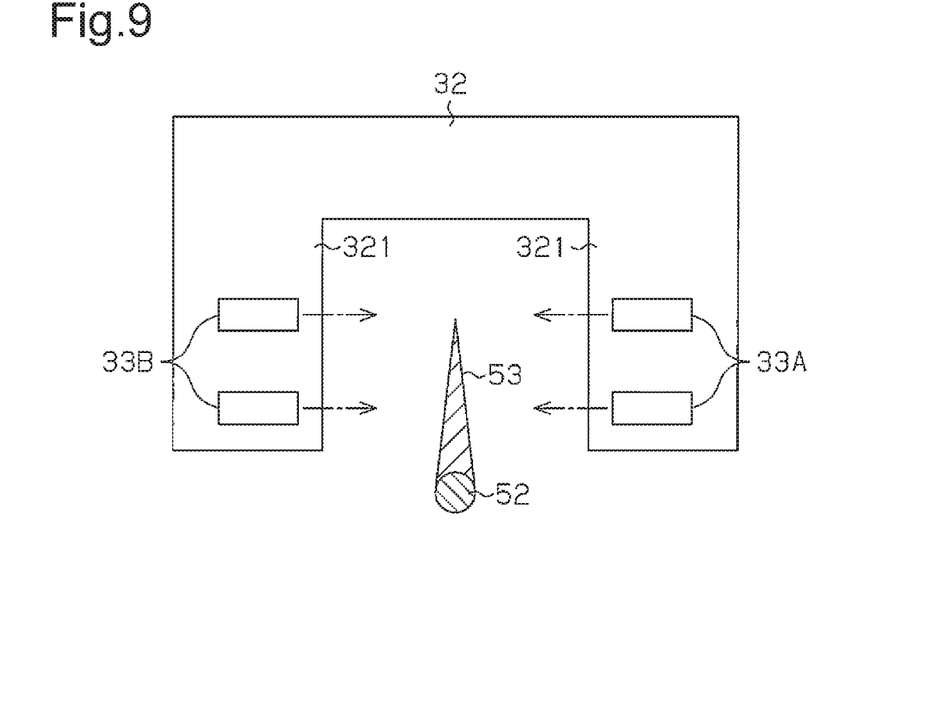
FIG. 9 is a partial side view showing a second embodiment of a filler connected portion inspection device.
Figure 10:
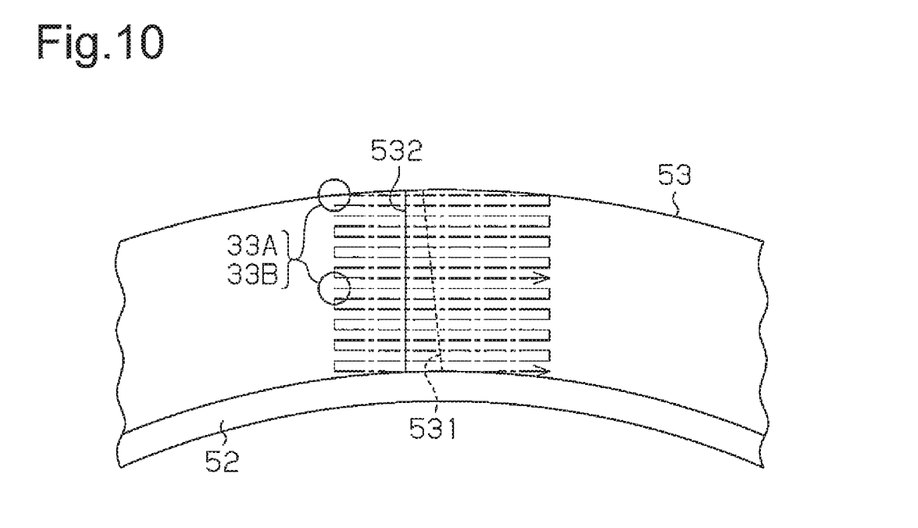
FIG. 10 is a partial front view showing optical scanning conducted on a connected portion of a filler by an optical sensor of the connected portion inspection device shown in FIG. 9.

In the second embodiment, as shown in FIGS. 9 and 10, among the two arms 321 of the scanning member 32, the front arm 321 supports two optical sensors 33A that are spaced apart in the vertical direction, and the rear arm 321 supports two optical sensors 33B that are spaced apart in the vertical direction. The two pairs of the optical sensors 33A and 33B are configured so that they can be opposed to the vicinity of the two end surfaces 531 and 532 at opposite sides of the filler 53. The optical scanning of the connected portion of the filler 53 by the optical sensors 33A and 33B is simultaneously performed on the region from the outer circumference to the middle of the filler 53 in the radial direction and the region from the middle to the inner circumference of the filler 53.

In addition to the advantages of the first embodiment, the second embodiment has the advantages described below.

(6) In the second embodiment, the optical sensors 33A and 33B that are spaced apart in the radial direction of the filler 53 perform optical scanning of the connected portion of the filler 53 simultaneously in a plurality of different regions arranged in the radial direction of the filler 53. This reduces the time used to inspect the state of the connected portion of the filler 53.

Modified Example

The above embodiments may be modified as described below.

Three or more optical sensors 33A and 33B may be arranged on each arm 321, and the optical scanning of the connected portion of the filler 53 may be simultaneously performed on three or more regions in the radial direction of the filler 53.

In each of the above embodiments, laser light is used to perform inspections. Instead, inspections may be performed through image processing that uses visible light.

DESCRIPTION OF REFERENCE CHARACTERS

22) support ring, 24) support, 26) first movable base, 28) second movable base, 30) third movable base, 32) scanning member, 33A and 33B) optical sensors, 35) movement cylinder, 36) reciprocation cylinder, 37) rotary disk, 38) crank rod, 39) pitch-feed motor, 43) ball screw, 45) controller, 46) memory, 48) display, L1) scanning range, L2) feed pitch.

The invention claimed is:

1. A filler connected portion inspection method for inspecting a connection state of two end surfaces of a strip of a filler adhered along an outer circumference of a bead core into an annular form, the filler connected portion inspection method comprising the steps of:
    attaching an annular assembled unit, which is configured by the bead core and the filler that is adhered along the outer circumference of the bead core, to an outer circumference of a support ring supported by a base;
    obtaining data of a distance from an optical sensor to a side surface of the filler by scanning a portion proximate to the two end surfaces at the side surface of the filler in a tangential direction of the filler over a predetermined scanning range with the optical sensor;
    repeating the step of obtaining data while changing a position of the optical sensor in a radial direction of the filler; and
    comparing the obtained data with reference data that is set in advance, wherein the step of obtaining data, the step of repeating, and the step of comparing are performed on two side surfaces of the filler.

2. The filler connected portion inspection method according to claim 1, wherein the two end surfaces of the filler are inclined relative to a thickness-wise direction of the filler.

3. The filler connected portion inspection method according to claim 1, wherein the two end surfaces of the filler extend parallel to a thickness-wise direction of the filler.

4. The filler connected portion inspection method according to claim 1, comprising the steps of:
   deriving a cross-sectional shape at the vicinity of the two end surfaces of the filler from the data obtained from the two side surfaces of the filler; and
   comparing the derived cross-sectional shape with a reference shape set in advance.

5. The filler connected portion inspection method according to claim 1, comprising the step of excluding data obtained from two ends of the scanning range.

\* \* \* \* \*